(12) United States Patent
Bolduc et al.

(10) Patent No.: US 11,589,862 B2
(45) Date of Patent: Feb. 28, 2023

(54) MULTI-FIRE FASTENER DELIVERY SYSTEM AND METHOD

(71) Applicant: Medtronic Vascular, Inc., Minneapolis, MN (US)

(72) Inventors: Lee Bolduc, Emerald Hills, CA (US); Joshua Stafford, Menlo Park, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 588 days.

(21) Appl. No.: 16/663,179

(22) Filed: Oct. 24, 2019

(65) Prior Publication Data

US 2020/0121319 A1 Apr. 23, 2020

Related U.S. Application Data

(62) Division of application No. 14/546,766, filed on Nov. 18, 2014, now Pat. No. 10,524,794.

(Continued)

(51) Int. Cl.
*A61B 17/068* (2006.01)
*A61B 50/30* (2016.01)
(Continued)

(52) U.S. Cl.
CPC ............ *A61B 17/068* (2013.01); *A61B 50/30* (2016.02); *A61B 17/105* (2013.01);
(Continued)

(58) Field of Classification Search
CPC ..... A61B 17/068; A61B 17/10; A61B 17/105; A61B 17/064; A61B 17/128;
(Continued)

(56) References Cited

U.S. PATENT DOCUMENTS

| 5,433,721 A | 7/1995 | Hooven et al. |
| 7,823,267 B2 | 11/2010 | Bolduc et al. |

(Continued)

FOREIGN PATENT DOCUMENTS

| CN | 102458267 A | 5/2012 |
| CN | 102802542 A | 11/2012 |

(Continued)

OTHER PUBLICATIONS

European Search Report, EP Application No. 14862952.0, dated Aug. 22, 2017, 16 pages.

(Continued)

*Primary Examiner* — Katherine H Schwiker
(74) *Attorney, Agent, or Firm* — Brooks Kushman P.C.

(57) ABSTRACT

A prosthesis fastener applier includes a handle, a plurality of input controls, and a fastener delivery shaft. The handle contains a motor and a control circuit. The input controls are connected to the handle and communicatively connected to the control circuit. The fastener delivery shaft includes a fastener cartridge and a driver shaft. The fastener cartridge includes a plurality of internal threads configured to receive a plurality of helical fasteners in stacked relationship. The driver shaft is operatively connected to the motor, disposed within the fastener cartridge, and configured to pass through respective inner diameters of the helical fasteners. The control circuit is configured to control the motor in response to signals from one or more of the input controls to rotate the driver shaft to cause one or more of the helical fasteners to be advanced axially relative to the fastener cartridge.

18 Claims, 13 Drawing Sheets

Related U.S. Application Data

(60) Provisional application No. 61/905,551, filed on Nov. 18, 2013.

(51) Int. Cl.
*A61B 17/00* (2006.01)
*A61B 17/064* (2006.01)
*A61B 90/00* (2016.01)
*A61B 17/10* (2006.01)

(52) U.S. Cl.
CPC .............. *A61B 2017/00115* (2013.01); *A61B 2017/00123* (2013.01); *A61B 2017/00398* (2013.01); *A61B 2017/00734* (2013.01); *A61B 2017/0649* (2013.01); *A61B 2090/0803* (2016.02)

(58) Field of Classification Search
CPC .......... A61B 17/1285; A61B 17/07207; A61B 2017/0649; A61B 2017/0688; A61B 2017/0647; A61B 2017/0648; A61B 2017/07235
See application file for complete search history.

(56) References Cited

U.S. PATENT DOCUMENTS

| | | |
|---|---|---|
| 8,231,639 B2 | 7/2012 | Bolduc et al. |
| 2004/0093057 A1 | 5/2004 | Bolduc et al. |
| 2006/0095119 A1 | 5/2006 | Bolduc |
| 2007/0073389 A1 | 3/2007 | Bolduc et al. |
| 2008/0086154 A1 | 4/2008 | Taylor et al. |
| 2009/0270976 A1 | 10/2009 | Douk et al. |
| 2010/0001038 A1 | 1/2010 | Levin et al. |
| 2010/0292712 A1 | 11/2010 | Nering et al. |
| 2011/0071578 A1 | 3/2011 | Colesanti et al. |
| 2011/0295282 A1 | 12/2011 | Glick et al. |
| 2012/0022557 A1 | 1/2012 | Cabiri et al. |
| 2013/0119108 A1 | 5/2013 | Altman et al. |
| 2013/0197591 A1 | 8/2013 | Corradi et al. |
| 2014/0309661 A1* | 10/2014 | Sheps ............... A61M 25/0108 606/130 |

FOREIGN PATENT DOCUMENTS

| | | |
|---|---|---|
| CN | 103338712 A | 10/2013 |
| EP | 1908409 A1 | 4/2008 |
| EP | 1990013 A1 | 12/2008 |
| EP | 2260775 A2 | 12/2010 |
| EP | 2389873 A2 | 11/2011 |
| JP | 10-506026 A | 6/1998 |
| JP | 2002-526193 A | 8/2002 |
| JP | 2008-093431 A | 4/2008 |
| JP | 2008-279255 A | 11/2008 |
| JP | 2011-245296 A | 12/2011 |
| WO | 98/56299 A1 | 12/1998 |
| WO | 00/16701 A1 | 3/2000 |
| WO | 2013/046115 A1 | 4/2013 |

OTHER PUBLICATIONS

Supplementary European Search Report, Application No. 14862952.0, dated May 4, 2018, pp. 1-18.

* cited by examiner

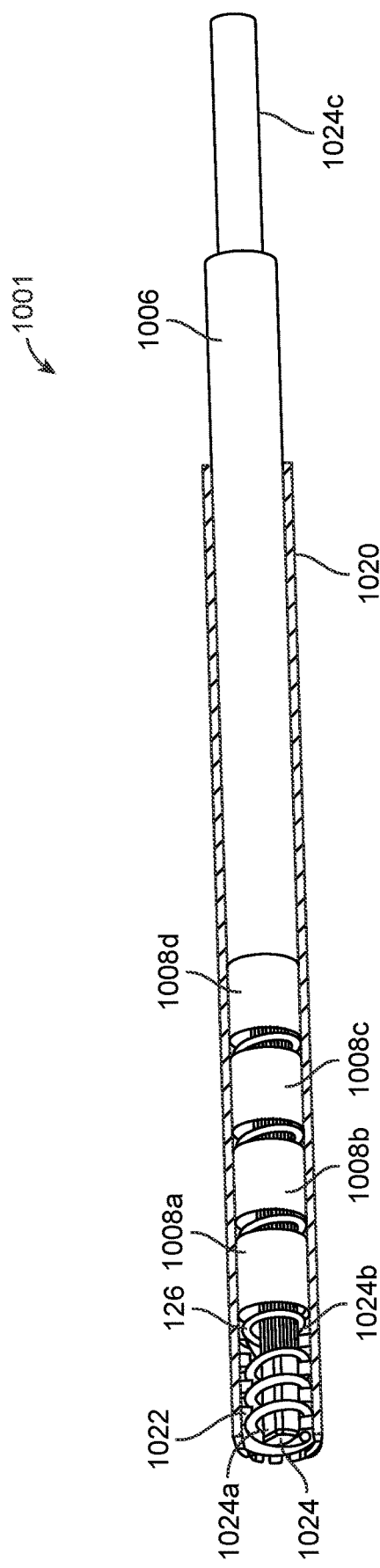
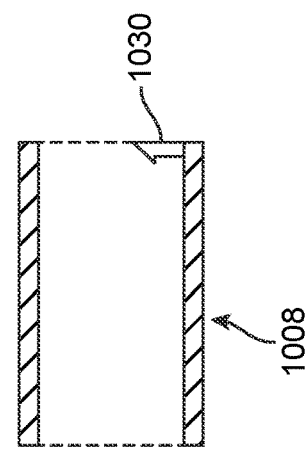
FIG. 10
FIG. 10A

MULTI-FIRE FASTENER DELIVERY SYSTEM AND METHOD

RELATED APPLICATION

This application is a divisional application of U.S. patent application Ser. No. 14/546,766, filed on Nov. 18, 2014, and issued as U.S. Pat. No. 10,524,794 on Jan. 7, 2020, which claims the benefit of U.S. Provisional Patent Application No. 61/905,551, filed Nov. 18, 2013, the benefit of priority of which is claimed hereby, and both of which are incorporated by reference herein in their entirety.

BACKGROUND

The weakening of a vessel wall from damage or disease can lead to vessel dilatation and the formation of an aneurysm. Left untreated, an aneurysm can grow in size and may eventually rupture.

For example, aneurysms of the aorta occur in the abdominal region, usually in the infrarenal area between the renal arteries and the aortic bifurcation. Aneurysms can also occur in the tortuous thoracic region between the aortic arch and renal arteries. The rupture of an aortic aneurysm results in massive hemorrhaging and has a high rate of mortality.

Damage or disease of a vessel such as the aorta may also result in a dissection of the vessel wall. Aortic dissections are usually caused by a connective tissue disorder and/or high blood pressure. Left untreated, an aortic dissection can rupture or critically reduce blood flow to the heart, the brain, the spinal cord, the abdominal organs and the legs.

SUMMARY

Examples according to this disclosure are directed to a fastener applier configured to hold and deliver multiple fasteners to secure a prosthesis disposed in an organ or vessel lumen. Multi-fire fastener appliers according to this disclosure are configured to be employed in open surgical procedures, instead of, for example, via an endovascular procedure.

In one example, a prosthesis fastener applier includes a handle, a plurality of input controls, and a fastener delivery shaft. The handle contains a motor and a control circuit. The input controls are connected to the handle and communicatively connected to the control circuit. The fastener delivery shaft includes a fastener cartridge and a driver shaft. The fastener cartridge includes a plurality of internal threads configured to receive a plurality of helical fasteners in stacked relationship. The driver shaft is operatively connected to the motor, disposed within the fastener cartridge, and configured to pass through respective inner diameters of the helical fasteners. The control circuit is configured to control the motor in response to signals from one or more of the input controls to rotate the driver shaft to cause one or more of the helical fasteners to be advanced axially relative to the fastener cartridge.

In another example, a fastener delivery shaft is disclosed. The prosthesis fastener delivery shaft includes a fastener cartridge, a driver shaft, and a plurality of projections. The fastener cartridge can comprise a plurality of internal threads configured to receive a plurality of helical fasteners in stacked relationship. The driver shaft can have a "D" shaped with a planar surface connected to a semicircular surface and a flexible intermediate portion. The driver can be disposed within the fastener cartridge and configured to pass through respective inner diameters of the helical fasteners. The plurality of projections can be disposed proximal of the fastener cartridge and arranged along a neutral axis of the fastener delivery shaft. The plurality of projections can be adapted to correspond with a pitch of the plurality of the helical fasteners to allow for reception and passage of one or more helical fasteners therealong. The driver shaft can be rotatable to cause one or more of the helical fasteners to be advanced axially relative to the plurality of projections to the fastener cartridge.

In another example, a fastener delivery shaft is disclosed. The prosthesis fastener delivery shaft includes a fastener cartridge, a driver shaft, and a helical member. The fastener cartridge can comprise a plurality of internal threads configured to receive a plurality of helical fasteners in stacked relationship. The driver shaft can have a "D" shaped with a planar surface connected to a semicircular surface and a flexible intermediate portion. The driver can be disposed within the fastener cartridge and configured to pass through respective inner diameters of the helical fasteners. The helical member can be disposed proximal of the of the fastener cartridge and can have a pitch adapted to correspond with that of the plurality of helical fasteners to allow for passage of one or more helical fasteners therealong. The driver shaft can be rotatable to cause one or more of the helical fasteners to be advanced axially relative to the helical member to the fastener cartridge.

In another example, a fastener delivery shaft is disclosed. The prosthesis fastener delivery shaft includes a fastener cartridge, a plurality of hollow storage members, and an advancement component. The plurality of storage members can be disposed proximal of the of the of the fastener cartridge. Each of the plurality of storage members can be adapted to receive and reside one or more of the plurality of helical fasteners therein. The advancement component can be moveable relative to the plurality of storage members to exert an advancement force on at least one of the plurality of helical fasteners to move the at least one helical fastener toward the fastener cartridge.

The details of one or more examples of the disclosure are set forth in the accompanying drawings and the description below.

BRIEF DESCRIPTION OF DRAWINGS

FIG. 10 depicts a distal end of an example multi-fire fastener applier in accordance with this disclosure. FIG. 10A is a cross-sectional view of a storage member having a barb, hook, or similar transfer feature at a proximal end in accordance with this disclosure.

DETAILED DESCRIPTION

Figure 1A:
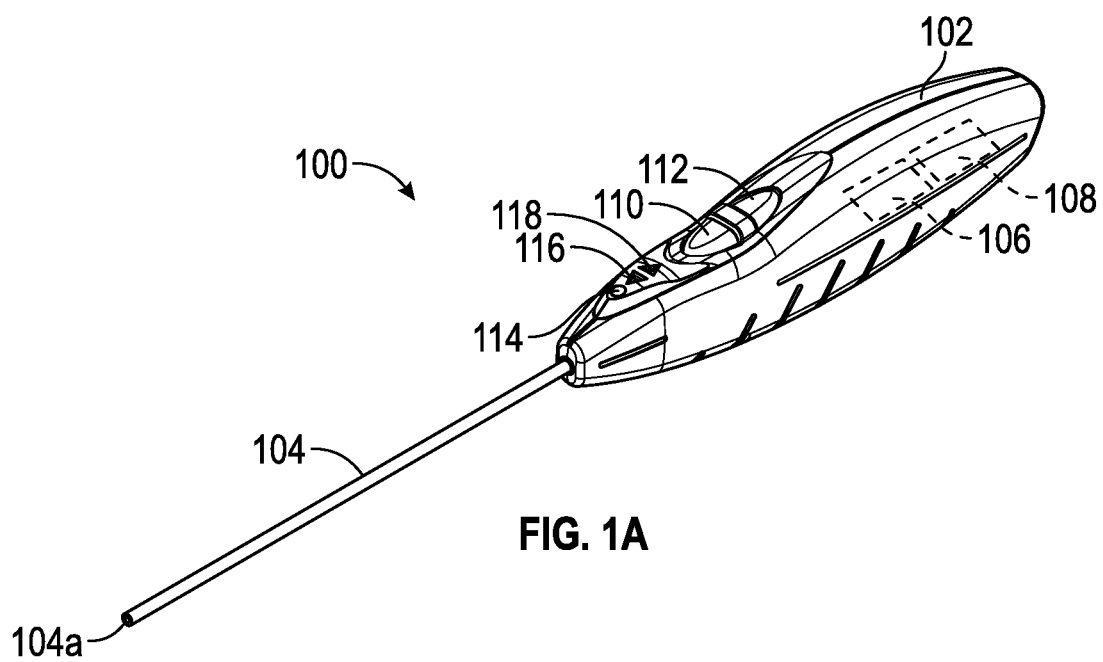
FIGS. 1A and 1B depict an example multi-fire fastener applier in accordance with this disclosure.

This specification discloses various devices, systems, and methods for delivering and implanting fasteners used to secure various prostheses and/or tissue as part of a vascular repair or other medical procedure. Examples according to this disclosure have application in procedures for the repair of diseased and/or damaged sections of a hollow body organ and/or blood vessel, including, e.g., repair of an aneurysmal section of the aorta.

Examples according to this disclosure are directed to a fastener applier configured to hold and deliver multiple fasteners to secure a prosthesis disposed in an organ or vessel lumen. Multi-fire fastener appliers according to this disclosure are configured to be employed in open surgical procedures, instead of, for example, via an endovascular procedure.

Example appliers include a handle from which extends a rigid fastener delivery shaft. The handle includes mechanisms for causing multiple fasteners to be delivered from the distal end of the shaft to a target site within a patient. The fastener delivery shaft can include a rigid outer sheath and an inner fastener cartridge, which is configured to hold a plurality of helical fasteners in a stacked arrangement within the cartridge. Extending longitudinally within the outer sheath and cartridge of the delivery shaft can be a fastener driver, which is configured to impart torque from an actuator of the applier to the fasteners within the shaft to cause the fasteners to penetrate and drive through a wall of a prosthesis and partially or completely through a body lumen within which the prosthesis is disposed.

Multi-fire appliers in accordance with this disclosure can be configured to sequentially deliver multiple fasteners, one-at-a-time to a target site selected by a physician. Each fastener delivered with a multi-fire applier according to this disclosure can be delivered in a manually, electronically, or partially manually and partially electronically controlled manner. For example, each fastener can be delivered via torque generated at a target level and/or for a specified amount of time or a specified number of revolutions by an electric motor, which is electronically controlled by a controller and user inputs provided in the handle of the applier. In some cases, the controller and motor system can include sensors, signals from which can be received by the controller or other processing devices to provide at least partial closed loop control of the motor. For example, the control circuit can be configured to estimate actual torque as a fastener is being delivered based on motor current. In the event a threshold torque value is exceeded the controller can interrupt operation of the motor and/or cause the motor to change direction, e.g., reverse the direction of the motor to start to back the fastener out of the prosthesis and/or the vessel wall.

In some cases, each fastener can be delivered from an example multi-fire applier in multiple phases. For example, the controller can be configured to deliver each fastener according to a multi-step algorithm, which includes multiple inputs from the physician via input controls on the applier and associated motor control signals from the controller to deploy the fastener in a series of phases or steps.

When referring to different structures in the examples according to this disclosure, including, e.g., an endovascular graft or its components and/or portions of a fastener delivery system, the terms "proximal" and "distal" are used to describe the relation or orientation of such structures with respect to a patient's heart after implantation. Therefore, the term "proximal" will be used to describe a relation or orientation of a structure that, when implanted, is toward the heart, and the term "distal" will be used to describe a position or orientation of the structure that, when implanted, is away from the heart, i.e., toward the feet.

When referring to implantation apparatus or devices that are manipulated by a physician or operator, the terms "proximal" and "distal" will be used to describe the relation or orientation of the apparatus or device with respect to the operator as it is used. Therefore, the term "proximal" will be used to describe a relation or orientation of the apparatus or device that, when in use, is positioned toward the operator (i.e., at the handle end of the device), and the term "distal" will be used to describe a position or orientation of the apparatus or device that, when in use, is positioned away from the operator (i.e., at the other end of a catheter or the like away from the handle).

Figure 1B:
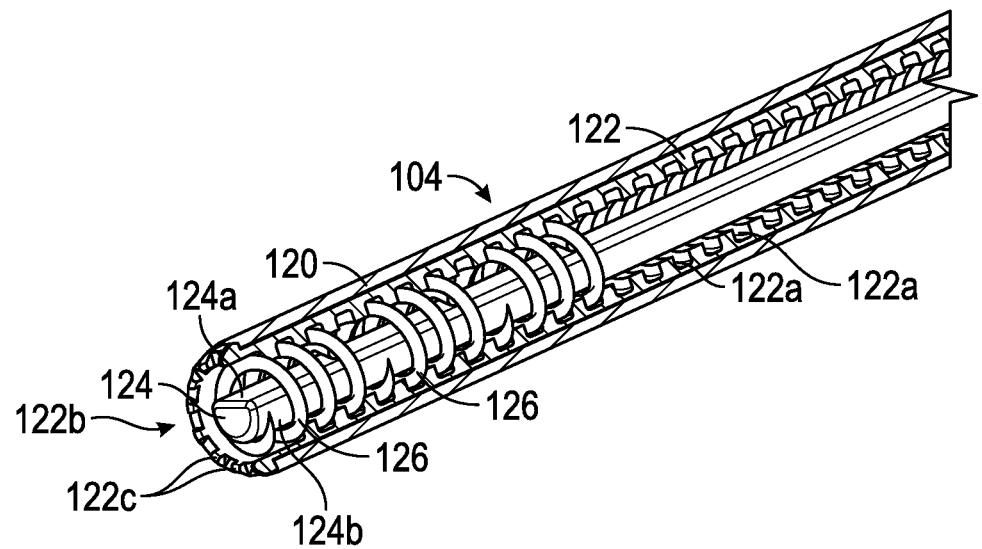

FIGS. 1A and 1B depict an example multi-fire fastener applier 100 in accordance with this disclosure. In some cases, applier 100 is a single use component that is supplied to the user within a package in a sterile condition. Additionally, multi-fire applier 100 and other such appliers in accordance with this disclosure can be provided to users in a kit along with other components, including, e.g., a supply of fasteners, and a cassette for holding and enabling the fasteners to be loaded into the applier.

In the example illustrated in FIGS. 1A and 1B, multi-fire applier 100 includes a handle 102 and fastener delivery shaft 104. Handle 102 includes a battery powered motor 106, control circuit 108, first and second control buttons 110 and 112, respectively, and indicators 114, 116, and 118. Delivery shaft 104 includes rigid sheath 120, fastener cartridge 122, and driver 124, each of which is radially inwardly nested one within the other such that fastener cartridge 122 is disposed within sheath 120 and driver 124 is disposed within cartridge 122. Cartridge 122 is sized and configured to hold a plurality of fasteners 126 in stacked relationship along the long axis of delivery shaft 104.

Figure 2A:
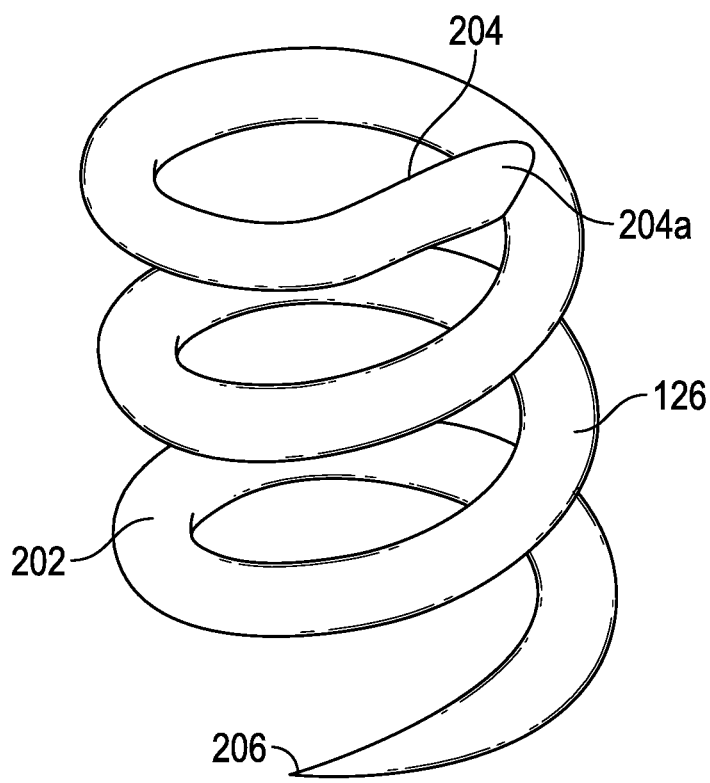
FIGS. 2A and 2B depict an example helical fastener and fastener cartridge in accordance with this disclosure.
Figure 2B:
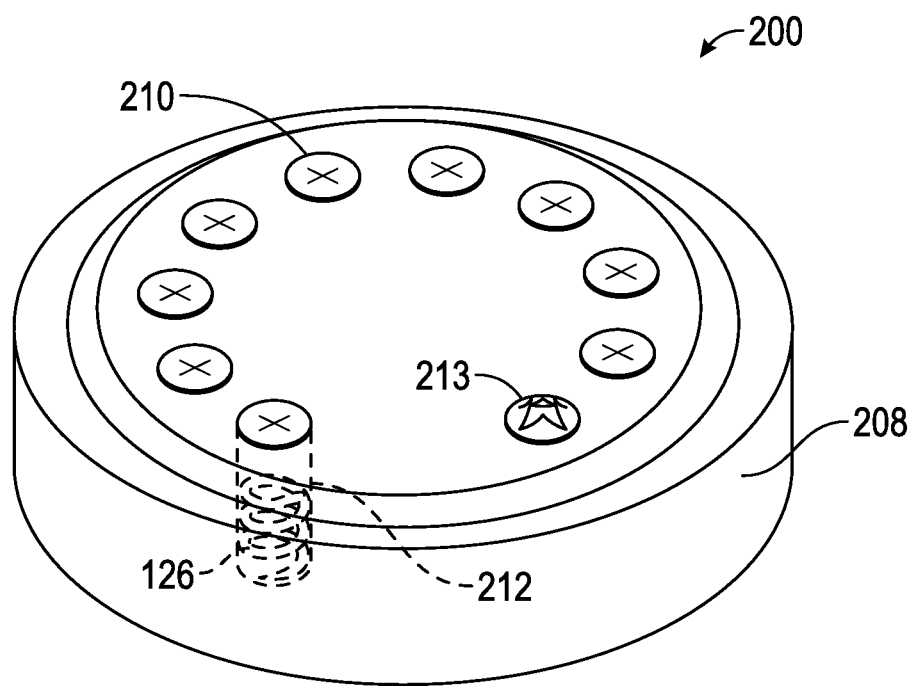

FIGS. 2A and 2B depict an example of helical fastener 126 and fastener cassette 200, respectively. Fastener 126 includes a helical main body 202 including a plurality of coils. Fastener 126 also includes a proximal cross-bar 204 and a distal tip 206 at either end of helical main body. Cassette 200 includes a base 208 and fastener ports 210 with associated deformable covers 212. Each of ports 210 is configured to house at least one helical fastener 126.

Delivery shaft 104 is configured to carry a plurality of fasteners 126 and driver 124 (shown in FIG. 1B), which can be rotationally driven to deliver fasteners 126 from the distal end 104a of shaft 104. Motor 106 enclosed within handle 102 is coupled to driver 124 within delivery shaft 104, to selectively rotate driver either in a forward (e.g., clockwise) direction and reverse (e.g., counterclockwise) direction. Control circuit 108 in handle 102 is coupled to motor 106 and to first, e.g., forward control button 110 and second, e.g., reverse control button 112 on handle 102. Control circuit 108 governs operation of motor 106 according to pre-programmed operating parameters in response to user commands received by manipulation of buttons 110 and 112.

In use, multiple helical fasteners 126 are loaded into delivery shaft 104, onto driver 124 from, e.g., cassette 200.

For example, a user can place distal end 104a of shaft 104 into an exposed staple port 210 in cassette 200 and press reverse control button 112 to signal control circuit 108 to drive motor 106 in a reverse direction to draw fastener 126 out of port 210 and into shaft 104, onto driver 124. This process can be repeated multiple times to load a plurality of fasteners 126 into shaft 104. The now loaded multi-fire applier 100 is manipulated by a user to dispose distal end 104a of shaft 104 through a surgical incision to access a desired location in a vessel for implantation of one or more fasteners 126. Once multi-fire applier 100, loaded with fasteners 126, is positioned at the desired location, the physician can push distal end 104a of shaft 104 against the wall of the prosthesis and the lumen within which the prosthesis is arranged to generate the force necessary to deploy one or more fasteners through the prosthesis and partially or completely through the lumen wall. Once the resolution (sometimes referred to as "apposition") force is achieved, the physician can press forward control button 110 to signal control circuit 108 to drive motor 106 in a forward direction to advance fastener 126 out of distal end 104a of shaft 104 through the prosthesis and into tissue.

Although examples of multi-fire applier 100 are described as used in conjunction with cassette 200 to load fasteners 126, in other examples, multi-fire applier 100 could be pre-loaded with a full set of fasteners 126 in fastener delivery shaft 104. For example, multi-fire applier 100 or another such applier in accordance with this disclosure can be packaged with a fixed or variable set number of fasteners 126 in delivery shaft 104 such that a physician need not load fasteners 126 at the time of surgery. In such examples, instead, the physician could remove multi-fire applier 100 from sterile packaging and start delivering fasteners 126 at desired locations without the need to load applier 100.

In one example, control circuit 108 is pre-programmed to require a two-stage implantation process. The first stage commands only a partial implantation of fastener 126. In the first stage, the physician is allowed to ascertain whether fastener 126 is placed correctly at the desired location and that the desired located is suitable for implantation of fastener 126. While in the first stage, the physician is allowed to retract fastener 126 (by pressing the reverse control button 112) and to re-position fastener 126.

Control circuit 112 can also be configured to command a full final deployment of fastener 126 only after a deliberate entry of the second stage. In the first and second stages, control circuit 112 can be configured, in some examples, to generate audible tones and/or visual indicators, e.g., by switching one or more of indicators 114, 116, and 118 on and off, during operation of motor 106, to indicate the position of fastener 126 and available direction of motion (e.g., forward and/or reverse).

As the one of the plurality of fasteners 126 in shaft 104 closest to distal end 104a is driven out of shaft 104, the other fasteners 126 are also advance toward distal end 104a along cartridge 122. Once the distal most fastener 126 is implanted, distal end 104a of fastener delivery shaft 104 can be repositioned to additional locations and the physician can repeat the process of delivering additional fasteners 126 at the locations with multi-fire applier 100.

Fastener 126 is a single use component that is supplied, in some cases, in companion cassette 200, to the user within a package in a sterile condition. Fastener 126 is sized and configured to attach a prosthesis, e.g., an endovascular graft to a vessel wall, and/or to close the entrance of a vessel dissection. As noted above, fastener 126 includes a main helical staple body 202. The helical-shape allows fastener 126 to pierce and engage tissue in response to rotation of main body 202, thereby securing attachment of, e.g., an endovascular graft to a vessel wall.

In one example, fastener 126 is manufactured from medical grade wire having a diameter between about 0.1 mm and 1.0 mm. In one example, fastener 126 is approximately between about 2 mm and 12 mm in over-all length and approximately between about 1.0 mm and 10 mm in maximum diameter. Distal tip 206 of main body 202 can be sharpened to facilitate atraumatic deployment through graft materials and vessel walls. Proximal end, including, cross-bar 204 of main body 202 can be closed to prevent over-penetration of fastener 126. In some examples, cross-bar 204 extends across the entire inner diameter of the proximal most coil of helical main body 202 and the extending end 204a of cross-bar 204 is connected to main body 202 such that the proximal end of fastener 126 does not have a terminating end, but, instead reconnects with itself. In one example, extending 204a of cross-bar 204 is welded to main body 202. Structurally connecting cross-bar 204 to main body 202 in this or another similar manner can provide the strength for necessary for fastener 126 to withstand the torque applied by driver 124 of multi-fire applier 100 to implant fastener 126 through a prosthesis and partially or completely through a lumen wall.

In one example, a plurality of fasteners 126 (e.g., ten) are provided in cassette 200, to allow easy and accurate loading into multi-fire applier 100. In one example, base 208 of cassette 200 has a plurality of foil covered spaced apart staple ports or stations 210, each sized to house a fastener 126. Deformable cover 212 (e.g. a foil cover) may be positioned over each staple port 210, and may include a precut shape, such as an "X". The precut "X" facilitates easy access for multi-fire applier 100 to fastener 126 within the port 210, and when the staple applier is inserted the deformable cover 212 and associate "X" deform 213, providing a visual indication to the user which port has been accessed.

Referring again to FIG. 1B, sheath 120 is fabricated from a rigid material. The "rigidity" of sheath 120, as used in this disclosure, refers to the ability of sheath 120 to withstand the force applied by a physician to resolve the force of implanting one of fasteners 126. For example, sheath 120 may need to be strong enough, e.g., have sufficient column strength to withstand the generally axial resolution force without buckling or being otherwise structurally compromised. A variety of biocompatible metals, plastics, or ceramics can be used to fabricate sheath 120, including, e.g., stainless steel, nickel-titanium (Nitinol), etc.

Fastener cartridge 122 includes a plurality of internal threads 122a. In examples including helical fastener 126, threads 122a can be helical threads with a pitch and diameter that corresponds to the pitch and diameter of fastener 126 such that fastener 126 can be threaded through cartridge 122, either to move a fastener 126 further proximally in the loading process of further distally in the delivery process. Cartridge 122 also includes crenellations 122c, which can decrease slipping of distal end 122b on the wall of the prosthesis against which multi-fire applier 100 is forced during implantation. Cartridge 122 can be fabricated from a variety of biocompatible materials. In some examples, cartridge 122 can add to the rigidity of shaft 104 by, e.g., being fabricated from rigid metals or plastics. In other examples, cartridge 122 can be fabricated from lighter weight, less rigid materials like silicone.

In some examples, driver 124 includes a "D" shaped elongated shaft with planar face 124a connected to semi-circular surface 124b. Driver 124 is shaped to fit within the inner diameters of fasteners 126. Additionally, driver 124 is configured to be disposed such that planar face 124a engages cross-bars 204 of fasteners 126 to transmit torque from driver 124 to fasteners 126. A variety of biocompatible metals, plastics, or ceramics can be used to fabricate driver 124, including, e.g., stainless steel, nickel-titanium (Nitinol), etc.

As illustrated in the example of FIG. 1B, cartridge 122 can include includes internal threads 122a, which terminate a predetermined distance from the distal end 122b of cartridge 122. Internal threads 122a engage fastener 126 when being loaded onto driver 124 and also partially drive fastener 126 out of shaft 104 and into tissue. For example, threads 122a of cartridge 122 terminate a predetermined distance from distal end 122b. This unthreaded portion of cartridge 122 provides an area in which fastener 126 can be rotated but not be driven out of distal end 104a of shaft 104.

The combination of threaded cartridge 122, centrally disposed driver 124, and the unthreaded distal end 122b of cartridge 122 function to facilitate proper delivery of fastener 124 such that fastener 124 penetrates a prosthesis and subsequently lumen wall. When fastener 126 is driven out of shaft 104 toward the prosthesis, if distal tip 206 of fastener 126 does not "bite" or, in other words, penetrate the prosthesis, then the fastener will simply spin within cartridge 122 without being advanced axially. At this point, the physician can apply additional resolution force to cause distal tip 206 of fastener to bite into the prosthesis. Once fastener 126 penetrates the prosthesis and tissue, further rotation of driver 124 rotates fastener 126 as before, except now the helical shape of fastener 126 in combination with the positive engagement of a portion of fastener with the prosthesis and then lumen wall cause fastener 126 to pull itself out of distal end 104a shaft. The unthreaded feature of cartridge 122 allows fastener 126 to pull itself out of shaft 104 when rotated by the driver only as long as fastener 126 has been previously engaged with the prosthesis and tissue. Additionally, the unthreaded distal end 122b of cartridge 122 ensures a more uniform depth of penetration for fastener 126, because fastener 126 drops off of threads 122a at substantially the same drop-off height each time.

Figure 3A:
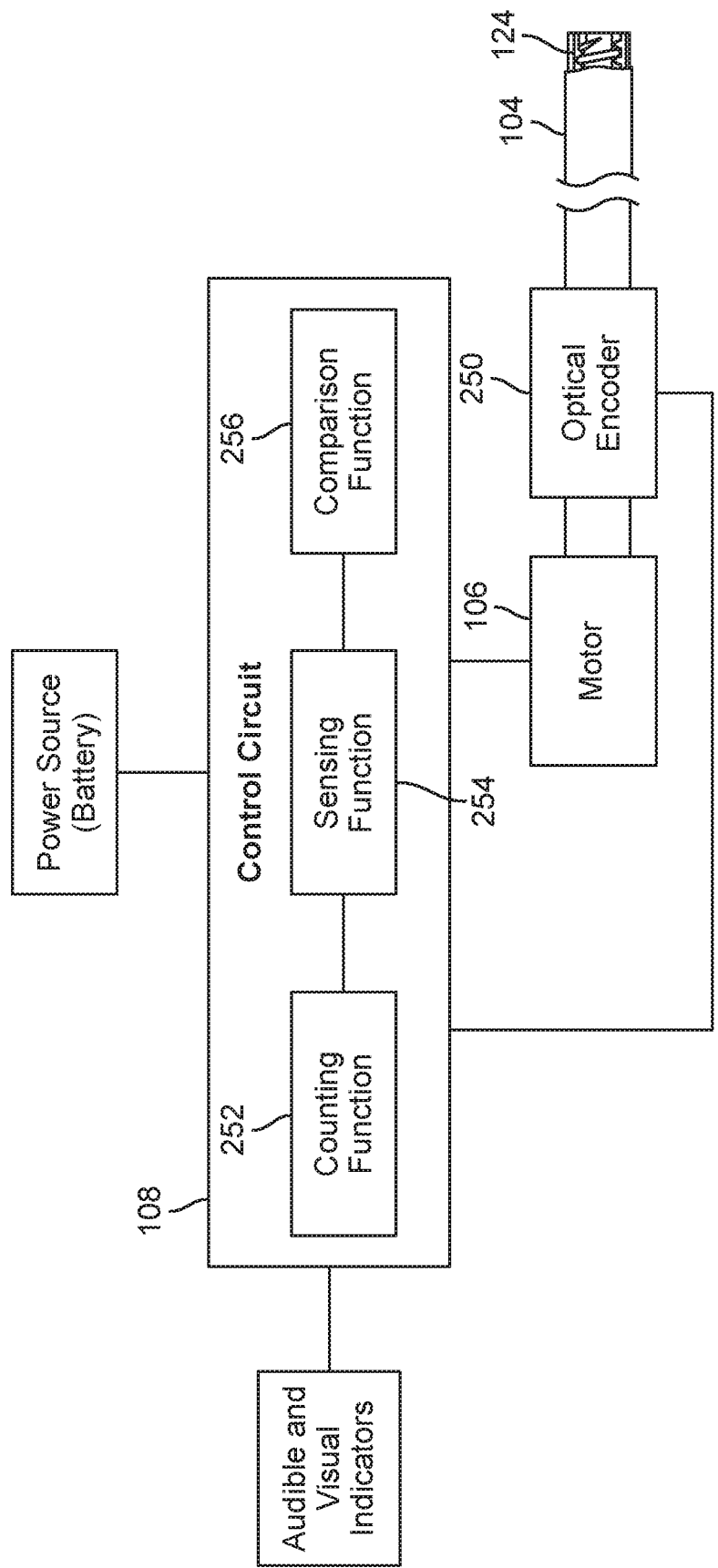
FIGS. 3A and 3B depict an example applier control circuit and example multi-phased operation of a multi-fire applier in accordance with this disclosure.
Figure 3B:
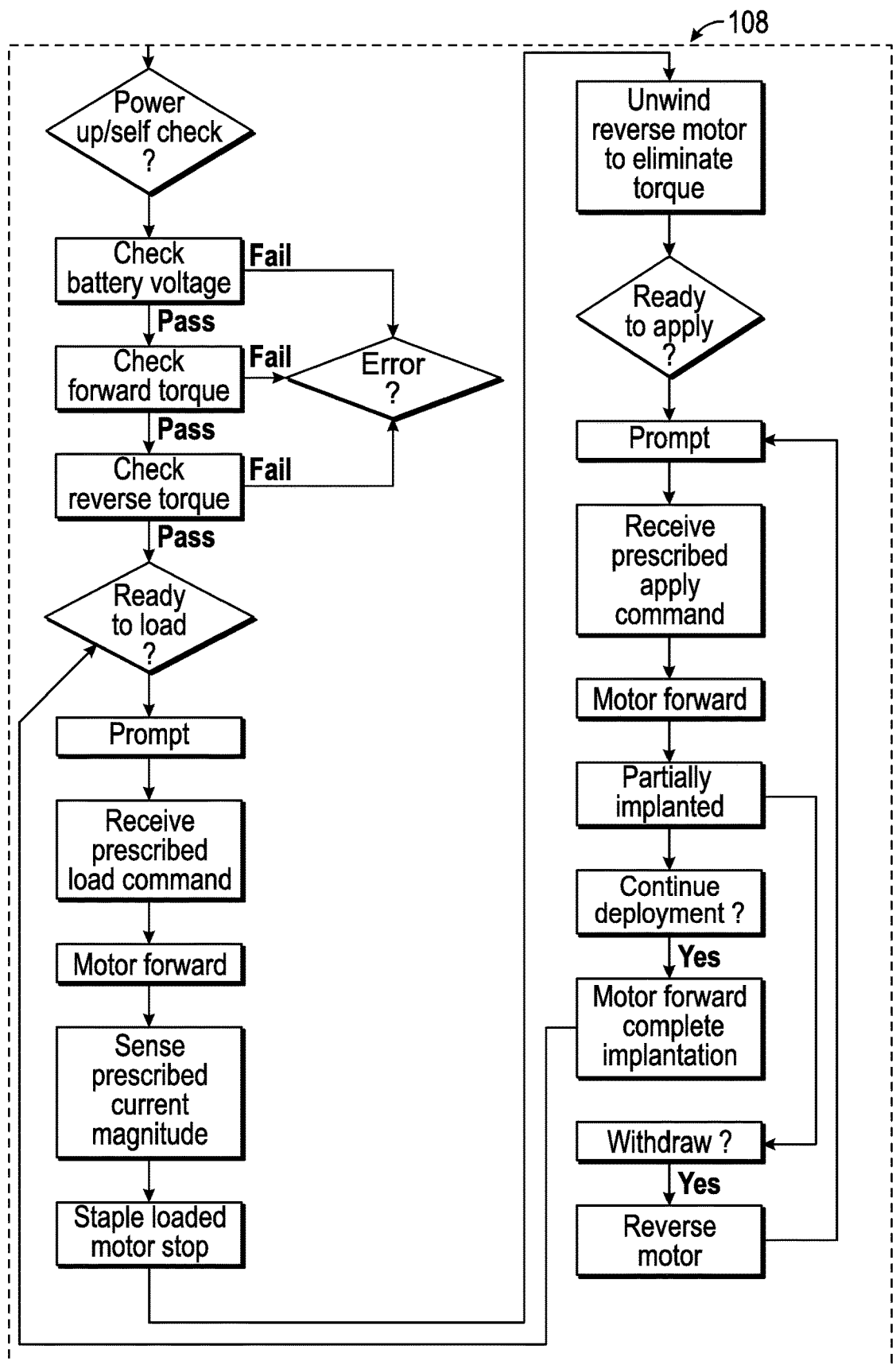

FIGS. 3A and 3B depict an example of control circuit 108 and an example multi-phased operation of multi-fire applier 100. As shown in FIG. 3A, motor 106 is coupled to apply torque to driver 124 of shaft 104. Control circuit 108 for motor 106 includes an optical encoder 250 coupled to a counting function 252, to enable counting the revolutions of the battery powered motor 106. Control circuit 108 also includes a sensing function 254 that senses the magnitude of current being drawn by motor 106, for deriving torque that motor 106 is encountering when rotating driver 124 to drive fasteners 126. Control circuit 108 also includes a comparison function 256 that compares the magnitude of the sensed torque (current) with set torque limits in either the forward or reverse direction, to change the state of operation should excess torque conditions be encountered.

Control circuit 108 carries embedded code, which expresses pre-programmed rules or algorithms under which different operation states are entered and motor command signals are generated in response to input from the external control sources and the counting, sensing, and comparison functions. The pre-programmed rules or algorithms of control circuit 108 are designed to conserve power consumption, placing the circuit into a standby (wait) mode between staple loading and deployment cycles. This makes it possible to power up the staple applier just once and to leave the staple applier on during an entire procedure, avoiding time consumed in repeated power ups and power downs. The pre-programmed rules or algorithms of the control circuit also dictate that a desired sequence of steps is faithfully followed in loading, deploying, and reloading the staples, prompting the physician at the initiation of each step and not allowing any short-cuts or deviations along the way.

Example pre-programmed rules and/or algorithms of a representative control circuit 108 for a multi-fire fastener applier in accordance with this disclosure will now be described in greater detail.

In one example, the pre-programmed rules or algorithms of control circuit 108 enter a POWER UP state when an operator enters a prescribed power up command, e.g., when the operator presses and holds the reverse control button 112 for a prescribed amount of time. In the POWER UP state, the pre-programmed rules or algorithms of control circuit 108 first check battery voltage against a set minimum. The POWER UP state proceeds if the battery voltage exceeds the set minimum. Otherwise, the pre-programmed rules or algorithms of control circuit 108 enter a LOW BATTERY FATAL state.

Absent a LOW BATTERY FATAL state, the pre-programmed rules or algorithms of control circuit 108 enable the optical encoder 250 and drive motor 106 in a forward direction for a set period of time. The counting and sensing functions of control circuit 108 count the number of revolutions and sense forward current. If the forward current exceeds a set maximum current level (as determined by the comparison function), the pre-programmed rules or algorithms of control circuit 108 enter a FORWARD TORQUE FATAL state. Otherwise, the sensed forward current is registered by the pre-programmed rules or algorithms of control circuit 108 as a base line for forward torque.

Absent a FORWARD TORQUE FATAL state, the pre-programmed rules or algorithms of control circuit 108 enable the optical encoder 250 and counting function 252, and drive motor 106 in a reverse direction for a set period of time. The counting function 252 of control circuit 108 counts the number of revolutions, while the sensing function 254 senses reverse current. If the reverse current exceeds a set maximum current level, as determined by the comparison function 256, the pre-programmed rules or algorithms of control circuit 108 enter a REVERSE TORQUE FATAL state.

Otherwise, the sensed reverse current is registered by the pre-programmed rules or algorithms of control circuit 108 as a base line for reverse torque.

Audible tones and visual indicators, e.g., indicators 114, 116, and 118, coupled to control circuit 108 can be accompany the POWER UP state as the system self-check is accomplished. If no fatal states are encountered during the POWER UP sequence, the pre-programmed rules or algorithms of control circuit 108 enter a READY TO LOAD state. The pre-programmed rules or algorithms of control circuit 108 enable a ready to load prompt, e.g., blinking a reverse green arrow indicator 118 (see FIG. 1A), to indicate to the user that multi-fire applier 100 is ready to load the first fastener 126. If a fatal state is encountered, the pre-programmed rules or algorithms of control circuit 108 enable a different prompt, e.g., illuminating a red error light 116 (see FIG. 1A), indicating that multi-fire applier 100 has encountered an error.

In addition, there are other checks that can be performed during the POWER UP state, including checking the encoder and the watchdog function for operation.

In one example, the pre-programmed rules or algorithms of control circuit 108 allow the operator to clear the error state one time, e.g., by pressing the forward control button 110. After the error has been cleared, the self-check sequence of the POWER UP state will reinitiate. If during the second self-check sequence, a fatal state is again encountered, the pre-programmed rules or algorithms of control circuit 108 either disable multi-fire applier 100 from use, or again enable the error prompt. In the latter instance, instructions for use can be provided to inform the operator not to use multi-fire applier 100 that has encountered a start-up error twice.

After multi-fire applier 100 has been powered up and is in the READY TO LOAD state, the operator is able to load fasteners 126 by initiating a prescribed input command, e.g., by pushing the reverse control button 112. Distal end 104a of fastener delivery shaft 104 can then be inserted into a staple port of the cassette at the time the input command is given.

When the prescribed input command is received, the pre-programmed rules or algorithms of control circuit 108 command motor 106 to rotate in a reverse direction for a set time period and generates a confirmation output with visual indicators (e.g., blinking the reverse green arrow 118). Fastener 126 will be drawn from cassette 200 into distal end 104a of fastener delivery shaft 104 of multi-fire applier 100.

The sensing function 254 of control circuit 108 senses the magnitude of the current drawn by motor 106 as fastener 126 is being loaded onto distal end 104a of shaft 104. Once a prescribed amount of current has been reached, the pre-programmed rules or algorithms of control circuit 108 consider multi-fire applier 100 to have completed the loading state. The pre-programmed rules or algorithms of control circuit 108 then automatically go into a UNWIND sequence, to reduce or eliminate amount of torque windup in shaft 104 of multi-fire applier 100 developed during the LOAD state. The pre-programmed rules or algorithms of the UNWIND sequence run motor 106 in the reverse direction from the load direction a set number of turns and wait for a command input.

After the UNWIND sequence, the foregoing load process can be repeated a predetermined number of times to fully load cartridge 122 with a prescribed number of fasteners 126. The pre-programmed rules or algorithms of control circuit 108 can include a predetermined number of loading cycles, after which the control presumes multi-fire applier 100 is fully loaded with a proper number of fasteners 126. The pre-programmed rules or algorithms of control circuit 108 can then enter a READY TO APPLY state. The pre-programmed rules or algorithms of control circuit 108 generate a confirmation output, e.g., audible and visual indicators (e.g., two short beeps and a forward green arrow 116 will blink to prompt the next step, which is to deploy fastener 126.

When the staple applier 38 has been powered up and is in the READY TO LOAD state, the pre-programmed rules or algorithms of control circuit 108, in one example, do not accept any command other than the command prescribed for loading (e.g., pushing the reverse control button 112). If an operator provides a contrary command, e.g., by pushing on the forward command button 110, the pre-programmed rules or algorithms of the command circuit 108 can ignore the command. In this way, the pre-programmed rules or algorithms of the command circuit can be configured to require an operator to follow a prescribed sequence in operating the staple applier.

When the pre-programmed rules or algorithms of control circuit 108 have entered the READY TO APPLY state, and the operator is ready to deploy fastener 126, the operator is able to deploy fastener 126 by initiating a prescribed input command, e.g., by pressing the forward control button 110. When the forward control button 112 is pushed, the pre-programmed rules or algorithms of control circuit 108 command motor 106 to rotate in a forward direction for a set number of rotations sensed by the counting function 252, which, according to the pre-programmed rules or algorithms, are less than the number of rotations required to fully implant fastener 126. The pre-programmed rules or algorithms of control circuit 108 suspend operation of motor 106 at this point and await another input command. Thus, the pre-programmed rules or algorithms of control circuit 108 only partially deploy fastener 126 and generate a confirmation output, e.g., four beeps and/or alternatively blinking the forward and reverse arrows 116 and 118, prompting the operator to make a choice. This indicates that the operator may chose to continue deployment or to withdraw fastener 126 back into multi-fire applier 100, as described above.

If the operator inputs a prescribed withdraw command, e.g., by pushing the reverse control button 112, the pre-programmed rules or algorithms of control circuit 108 drive motor 106 in the reverse direction for a set number of rotations sensed by the counting function 252, to withdraw fastener 126. The pre-programmed rules or algorithms of control circuit 108 can then return to the READY TO APPLY state.

If the operator inputs a prescribed complete the implantation command, e.g. by pushing the forward control button 110, the pre-programmed rules or algorithms of control circuit 108 can be configured to drive motor 106 in the forward direction for a set number of rotations monitored by the counting function 252, to complete the implantation of fastener 126. The pre-programmed rules or algorithms of control circuit 108 generate a confirmation output, e.g., audio and visual indicators. The pre-programmed rules or algorithms of control circuit 108 return to the READY TO APPLY state to repeat the deployment procedure to implant a plurality of fasteners 126. Additionally, the pre-programmed rules or algorithms of control circuit 108 can include a predetermined number of delivery cycles for delivering all of fasteners 126 in multi-fire applier 100, after which the control circuit can return to the READY TO LOAD state.

During the different operational states, the pre-programmed rules or algorithms of control circuit 108 can be configured to continue to check battery voltage against a set minimum. The operational states proceed as described as long as the battery voltage exceeds the set minimum. If, during an operational state the battery voltage falls below the set minimum, the pre-programmed rules or algorithms of control circuit 108 can be configured to enter a LOW BATTERY FATAL state.

As noted above, in other examples, multi-fire applier 100 is pre-loaded with a full set of fasteners 126 in fastener delivery shaft 104. For example, multi-fire applier 100 can be packaged with a fixed or variable set number of fasteners 126 (e.g., different numbers of fasteners packaged in different fastener delivery systems) in delivery shaft 104 such that a physician need not load fasteners 126 at the time of surgery. In such examples, the pre-programmed rules or algorithms of control circuit 108 may be adjusted to remove the need for the fastener loading process described above.

In one example, audible tones and visual indicators, e.g., indicators 114, 116, and 118, coupled to control circuit 108 can accompany the POWER UP state as the system self-check is accomplished. If no fatal states are encountered during the POWER UP sequence, the pre-programmed rules or algorithms of control circuit 108 enter a READY TO APPLY state. When the pre-programmed rules or algorithms of control circuit 108 have entered the READY TO APPLY state, and the operator is ready to deploy fastener 126, the operator is able to deploy fastener 126 by initiating a prescribed input command, e.g., by pressing the forward control button 110.

When the forward control button 112 is pushed, the pre-programmed rules or algorithms of control circuit 108 command motor 106 to rotate in a forward direction for a set number of rotations sensed by the counting function 252, which, according to the pre-programmed rules or algorithms, are less than the number of rotations required to fully implant fastener 126. The pre-programmed rules or algorithms of control circuit 108 suspend operation of motor 106 at this point and await another input command. Thus, the pre-programmed rules or algorithms of control circuit 108 only partially deploy fastener 126 and generate a confirmation output, e.g., four beeps and/or alternatively blinking the forward and reverse arrows 116 and 118, prompting the operator to make a choice. This indicates that the operator may chose to continue deployment or to withdraw fastener 126 back into multi-fire applier 100, as described above.

If the operator inputs a prescribed withdraw command, e.g., by pushing the reverse control button 112, the pre-programmed rules or algorithms of control circuit 108 drive motor 106 in the reverse direction for a set number of rotations sensed by the counting function 252, to withdraw fastener 126. The pre-programmed rules or algorithms of control circuit 108 can then return to the READY TO APPLY state.

If the operator inputs a prescribed complete the implantation command, e.g. by pushing the forward control button 110, the pre-programmed rules or algorithms of control circuit 108 can be configured to drive motor 106 in the forward direction for a set number of rotations monitored by the counting function 252, to complete the implantation of fastener 126. The pre-programmed rules or algorithms of control circuit 108 generate a confirmation output, e.g., audio and visual indicators. The pre-programmed rules or algorithms of control circuit 108 return to the READY TO APPLY state to repeat the deployment procedure to implant a plurality of fasteners 126. Additionally, the pre-programmed rules or algorithms of control circuit 108 can include a predetermined number of delivery cycles corresponding to the number of fasteners 126 pre-loaded in multi-fire applier 100.

Further details of representative constructions of multi-fire delivery system and methods of its use in accordance with this disclosure, including features of the pre-programmed rules or algorithms of a representative control circuit, can be found in co-pending, commonly owned U.S. Pat. No. 7,823,267, filed Oct. 20, 2005, and entitled "DEVICES, SYSTEMS, AND METHODS FOR PROSTHESIS DELIVERY AND IMPLANTATION, INCLUDING THE USE OF A FASTENING TOOL," U.S. patent application Ser. No. 11/488,305, filed Jul. 18, 2006, and entitled "ENDOVASCULAR ANEURYSM DEVICES, SYSTEMS, AND METHODS," and U.S. Pat. No. 8,231,639, filed Feb. 25, 2004, and entitled "SYSTEMS AND METHODS FOR ATTACHING A PROSTHESIS WITHIN A BODY LUMEN OR HOLLOW ORGAN," the entire contents of all of which are incorporated herein by reference.

The devices, systems, and methods in accordance with this disclosure can be employed for treating aortic dissections and aneurysms of the aorta, including those that occur in the thoracic region between the aortic arch and renal arteries, as well as aneurysms that also occur in the abdominal region, usually in the infrarenal area between the renal arteries and the aortic bifurcation. Some of the conditions for which examples according to this disclosure can be used are described below with reference to FIGS. 4-6B. However, the disclosed devices, systems, and methods are applicable for use in treating other dysfunctions elsewhere in the body, which are not necessarily aorta-related or specifically described below and illustrated in the associated figures.

Figure 4:
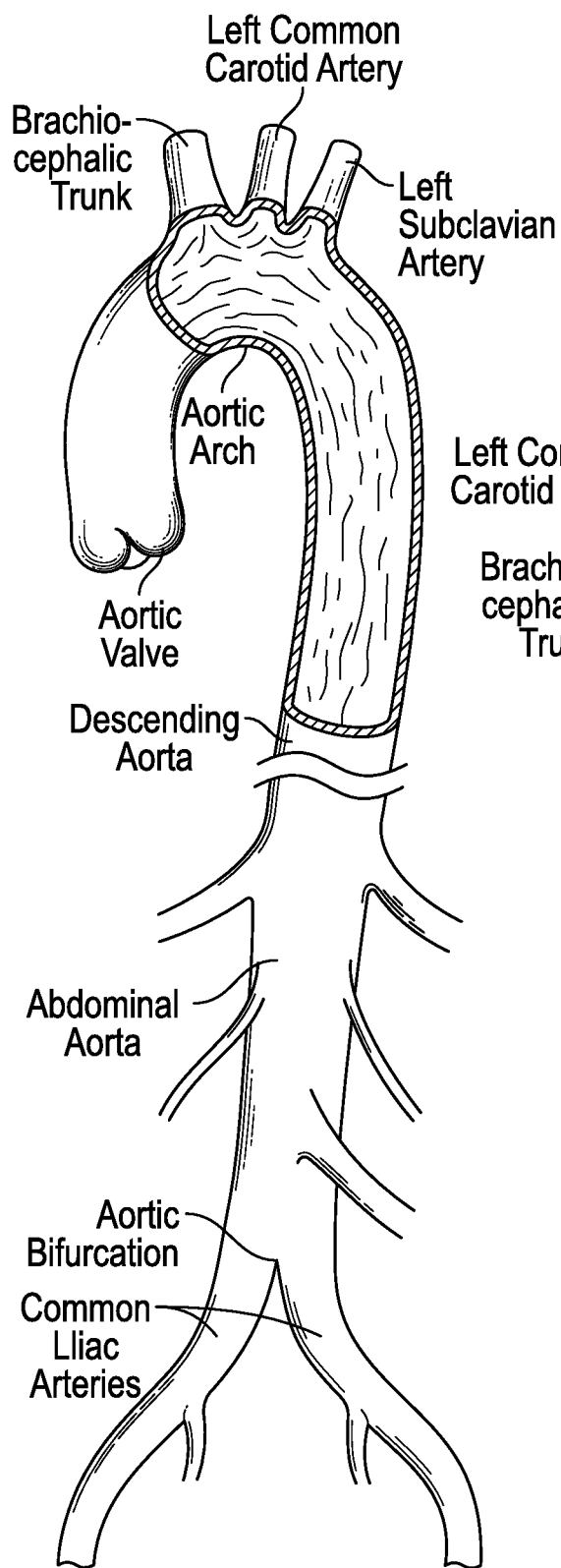
FIG. 4 is a perspective view of a healthy aorta showing the extent of the aorta from the aortic root, through the aortic arch, the descending thoracic aorta, and to the abdominal aorta and aortic bifurcation.

A healthy aorta, the body's largest artery, has a general shape like the handle portion of a walking cane (see FIG. 4). The short length of the curved handle comes out of the heart and curls through the aortic arch. Multiple smaller arteries branch off at the aortic arch to serve the head and arms. The aorta continues to descend through the chest cavity into the abdomen and separates to provide blood to the abdominal organs and both legs. Various abnormalities may affect the aorta, most of which are considered potentially life-threatening. Prevalent aortic abnormalities include aortic aneurysms and aortic dissections, as non-limiting examples.

Figure 5A:
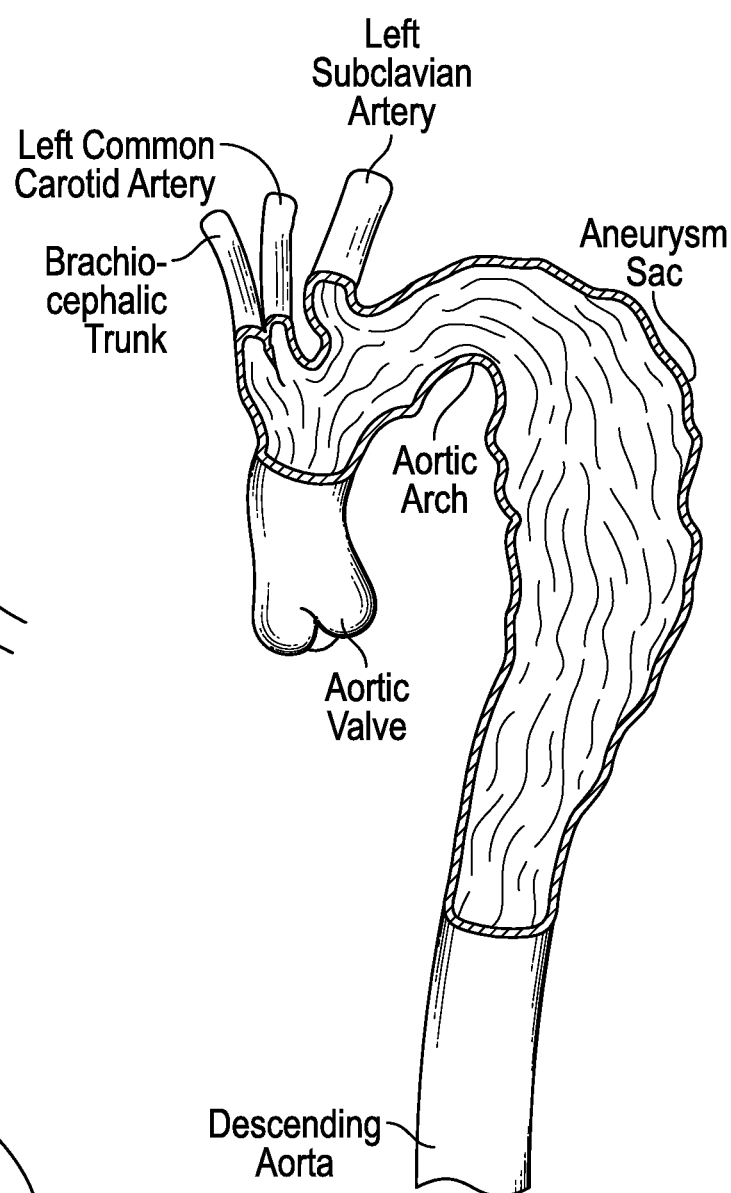
FIGS. 5A, 5B, and 5C are perspective views of diseased aortas, showing the extent to which aneurysms may deform the aorta.
Figures 5B, 5C:
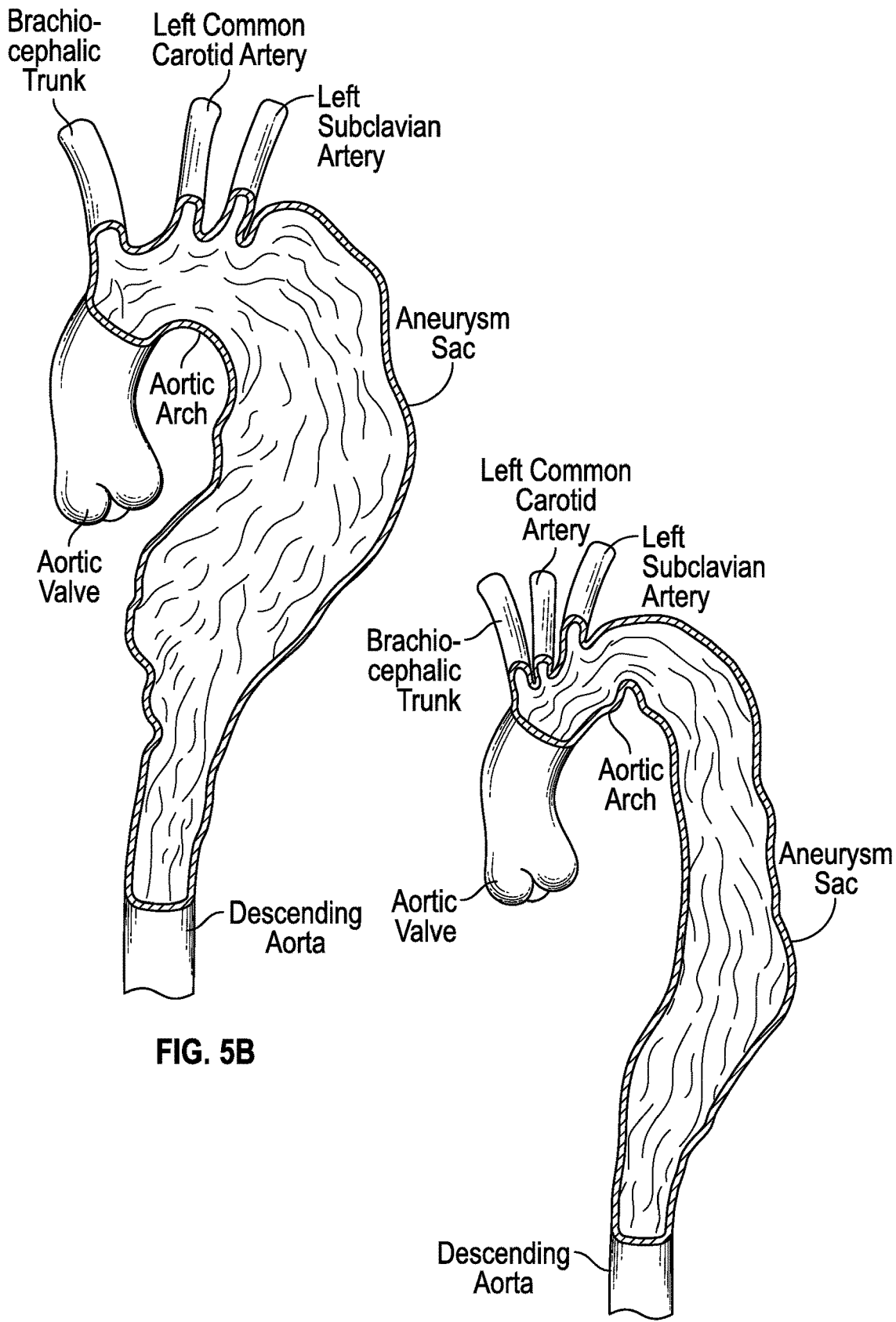

Aneurysms may affect one or more segments of the thoracic aorta, including the ascending aorta, the arch, and the descending thoracic aorta. A thoracic aortic aneurysm (TAA) can be described as an expanded (bulging) section(s) of the wall of the aorta, and is considered a life-threatening condition. Thoracic aortic aneurysms of any size can cause significant short- and long-term mortality due to rupture and dissection. FIGS. 5A to 5C show examples of aortas having diseased tissues and difficult cases where the left subclavian artery ostium is distal to the aortic arch. Relative positions of the aneurysmal tissues in the tortuous aortic arch can be seen, as can and relationship to the brachiocephalic trunk, left common carotid artery, and the left subclavian artery. Often the left subclavian artery provides a landmark for positioning of an endovascular graft (to be described in greater detail below).

Common causes of a thoracic aortic aneurysm include hardening of the arteries (atherosclerosis), degeneration of the media of the aortic wall, as well as from local hemodynamic forces. Additional risk factors include various connective tissue disorders such as Marfan syndrome, previous dissection of the aorta, and trauma such as falls or motor vehicle accidents. They also sometimes occur in people who have bicuspid aortic valves.

Figure 6A:
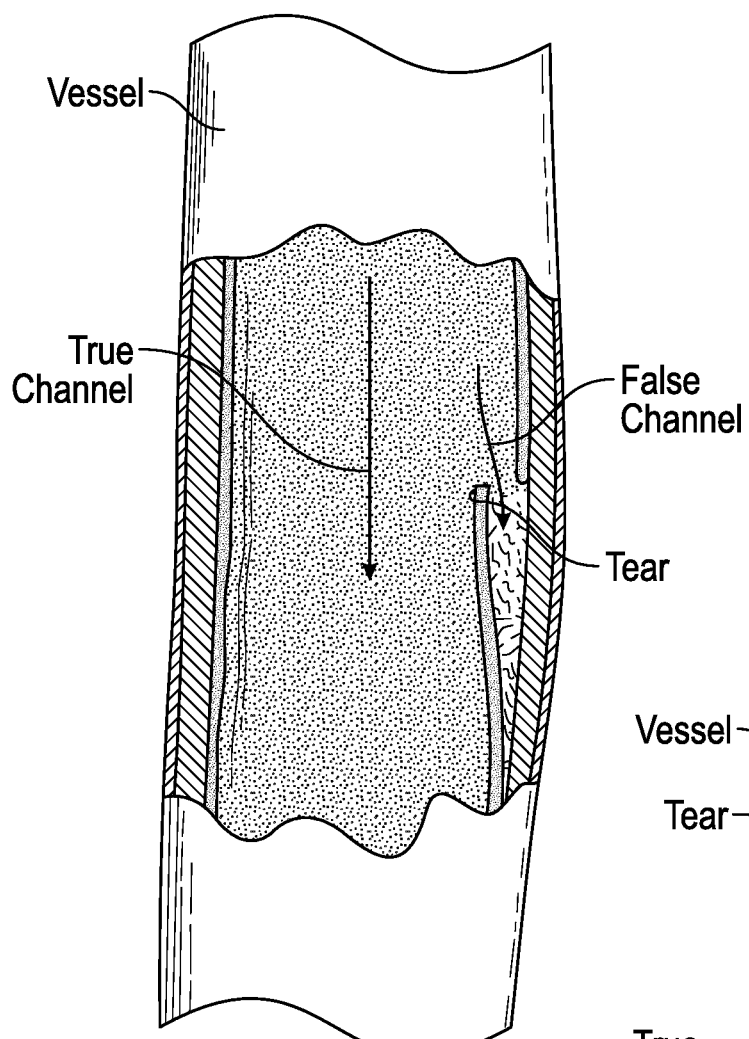
FIGS. 6A and 6B are perspective views of diseased aortas, showing aortic dissections.
Figure 6B:
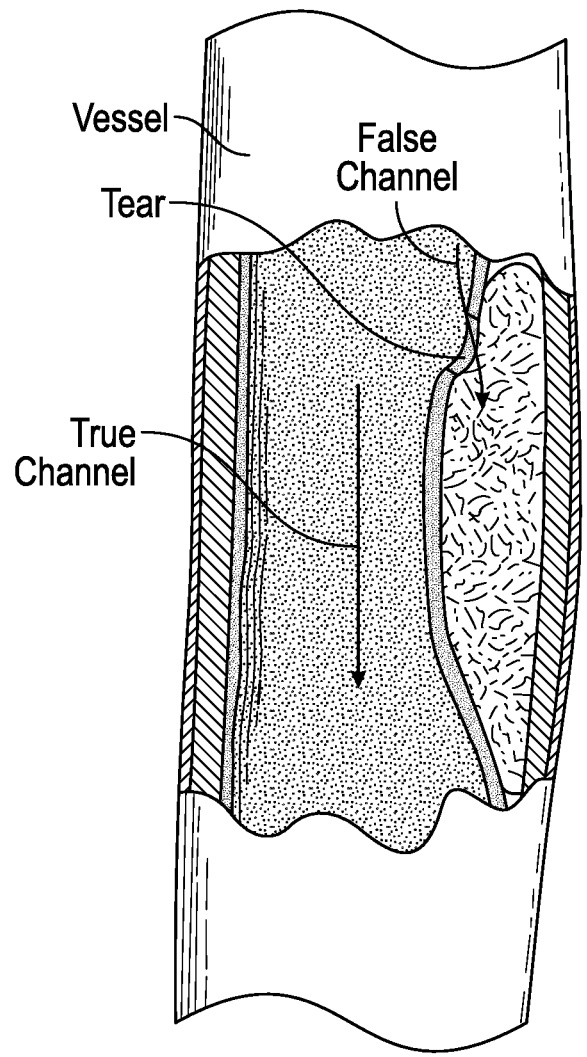

An aortic dissection is a perforation or tear in the lining of the aorta. The tear allows blood to flow between the layers of the aortic wall, with the force of the blood forcing the layers of the wall apart. FIGS. 6A and 6B show views of aortic dissections. An aortic dissection is a medical emergency and can quickly lead to death. If the dissection tears the aortic wall completely open, massive and rapid blood loss occurs.

The tearing of the inner lining of the aorta causes the blood to separate along the wall of the artery. This generally causes two channels in the vessel, with one channel referred to as the true channel and the other channel referred to as the false channel. As can be seen in FIGS. 6A and 6B, the tear allows the blood to create the false channel. With each heartbeat, the artery may progressively tear more and more with blood propagating down the false channel blocking off the true channel and the flow of blood to some or all of the branches of the aorta.

Aortic dissections can be classified by the Stanford method into a type A or type B depending on the location and the extent of the dissection. Type A dissection, or proximal dissection, involves the ascending aorta and aortic arch, and may or may not involve the descending aorta. Type B dissection, or distal dissection, usually begins just distal to the ostium of the left subclavian artery, extending distally into the descending and abdominal aorta. If left untreated, the risk of death from aortic dissection can reach 30 percent within fifteen minutes after onset of symptoms and 75 percent by one week.

Figure 7A:
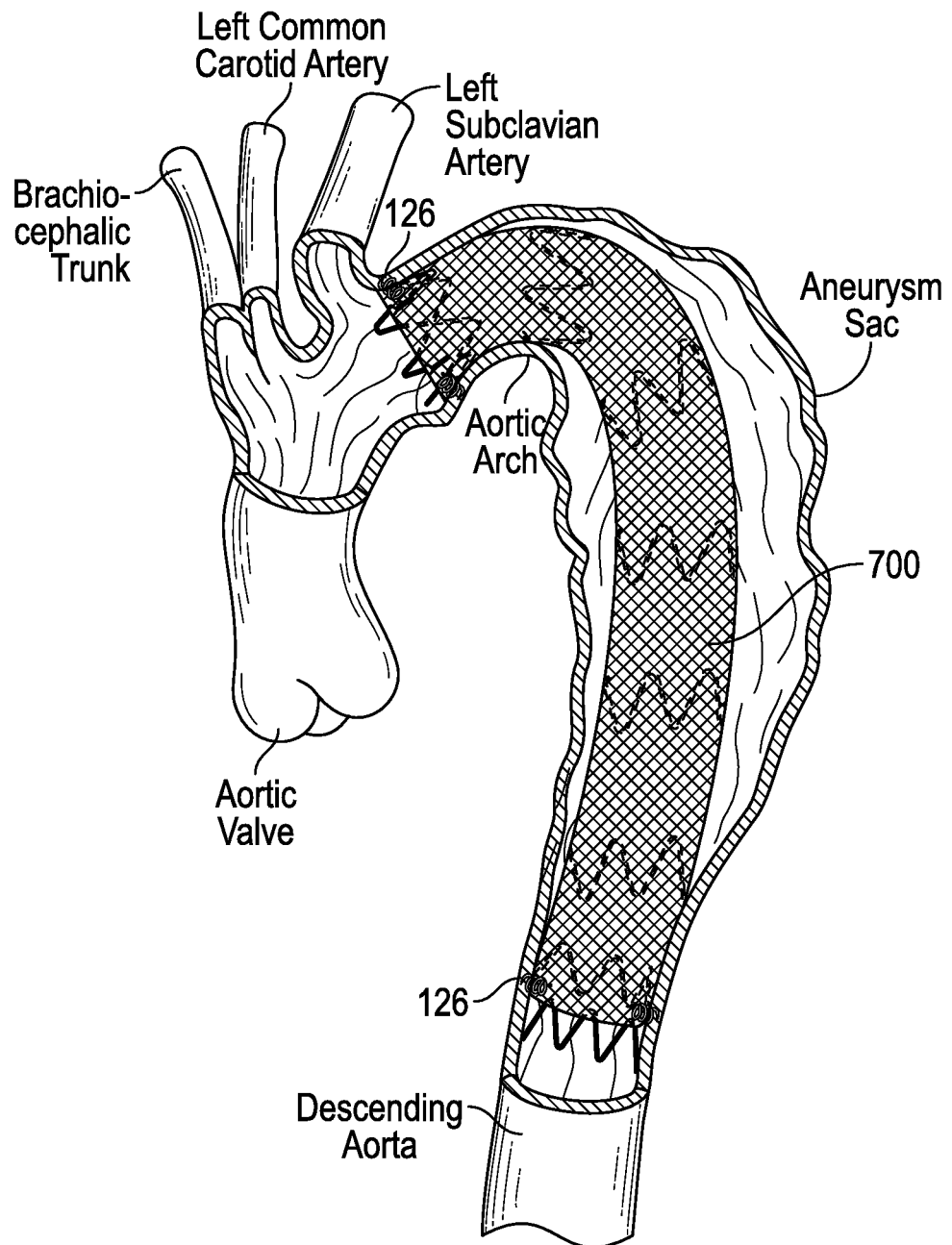
FIGS. 7A and 7B illustrate an endovascular graft implanted within the aorta to treat aortic aneurysms and dissections, respectively, and secured with helical fasteners implanted with a multi-fire delivery system in accordance with this disclosure.
Figure 7B:
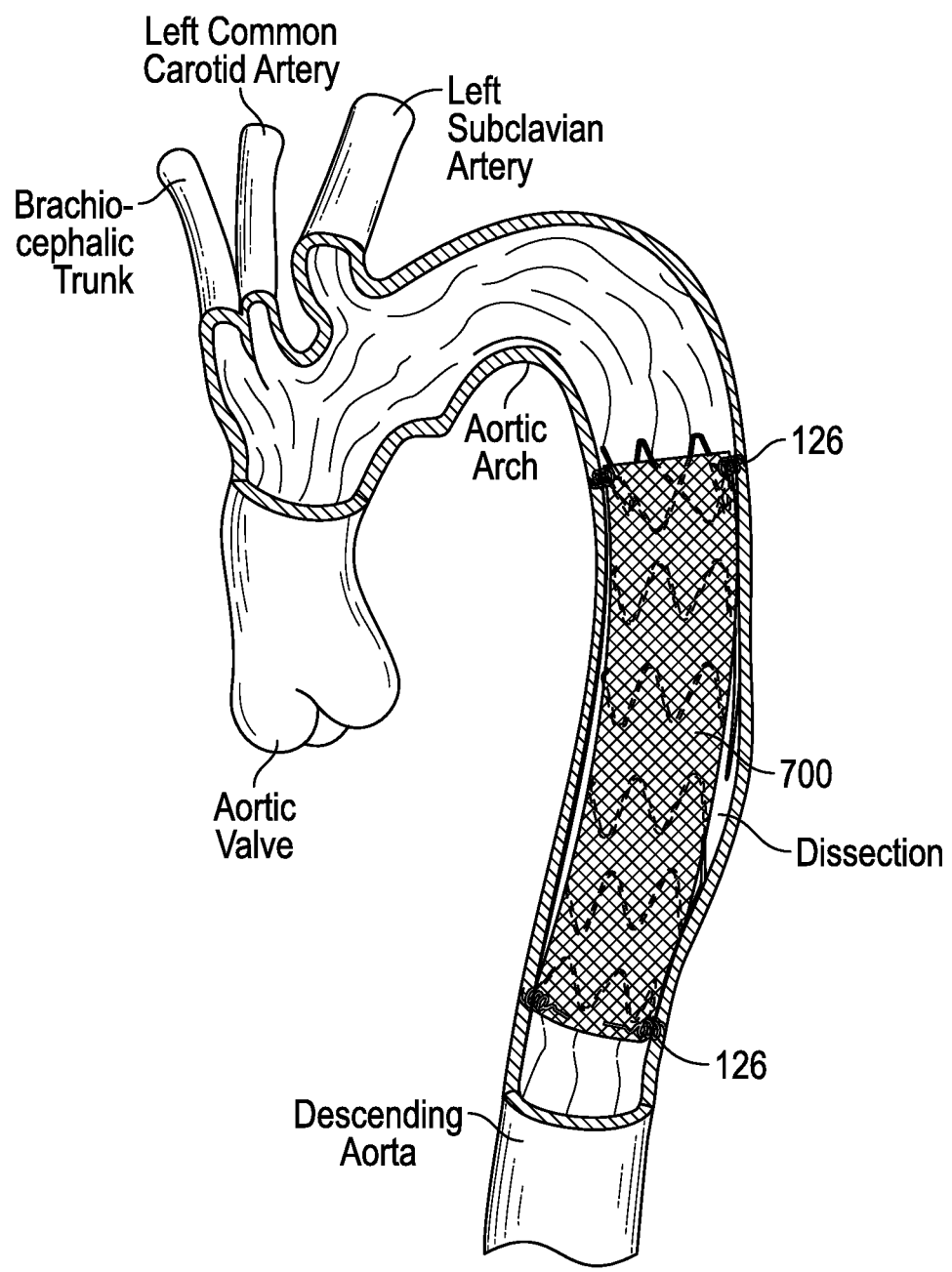

FIGS. 7A and 7B illustrate an endovascular graft implanted within the aorta to treat an aortic aneurysm and dissection, respectively, and secured with helical fasteners implanted with a multi-fire delivery system in accordance with this disclosure. Aortic abnormalities, such as thoracic aortic aneurysms and aortic dissections with the appropriate anatomy, can be repaired by the implantation of an endovascular prosthesis or graft 700. The implantation of staples alone may also be used for the repair of aortic dissections. In use, the endovascular graft 700 is placed within a vessel at the site of the aortic abnormality. The endovascular graft 700 serves to exclude a portion of the vascular system from blood flow and blood pressure. In order to obtain exclusion of a portion of the vascular system, the endovascular graft must be sealed against the vascular wall, which requires apposition between the endovascular graft 700 and the vascular wall. The endovascular graft 12 may need to be prevented from moving or migrating from its deployed position within the vascular system.

In the illustrated embodiments, the endovascular graft 700 is placed and secured within the aortic arch by a number of fasteners 126, e.g., at or near the left subclavian artery and extends past the site of the aneurysm and into the descending aorta (see FIG. 7A). Fasteners 126 can be implanted to secure graft 700 employing a multi-fire fastener applier in accordance with this disclosure in a manner similar to the examples provided above. FIG. 7B shows the endovascular graft 700 placed and secured within the descending aorta and extending past the site of a dissection.

Figure 8:
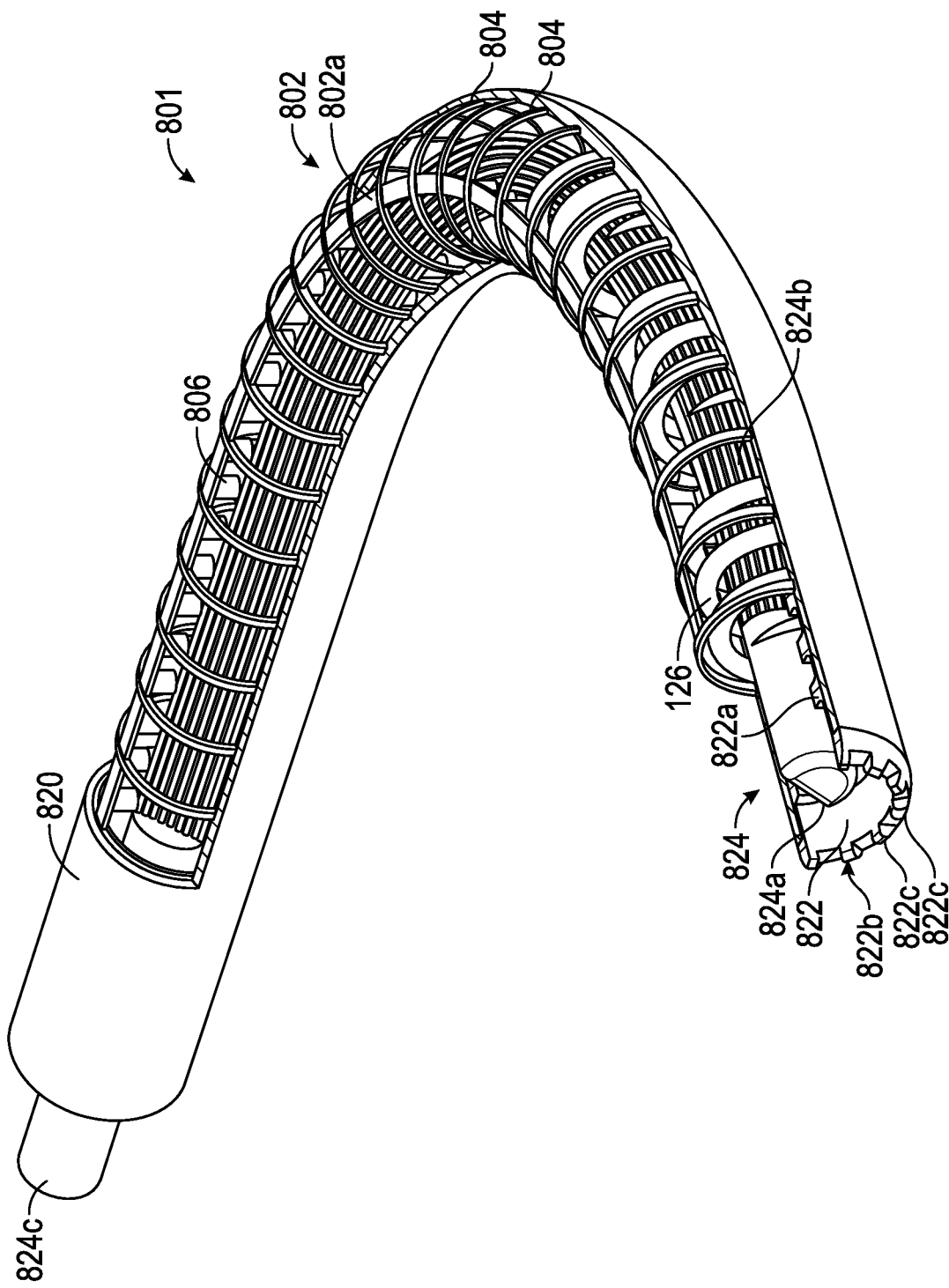
FIGS. 8, 8A, and 8B depict a distal end of an example multi-fire fastener applier in accordance with this disclosure.
Figure 8A:
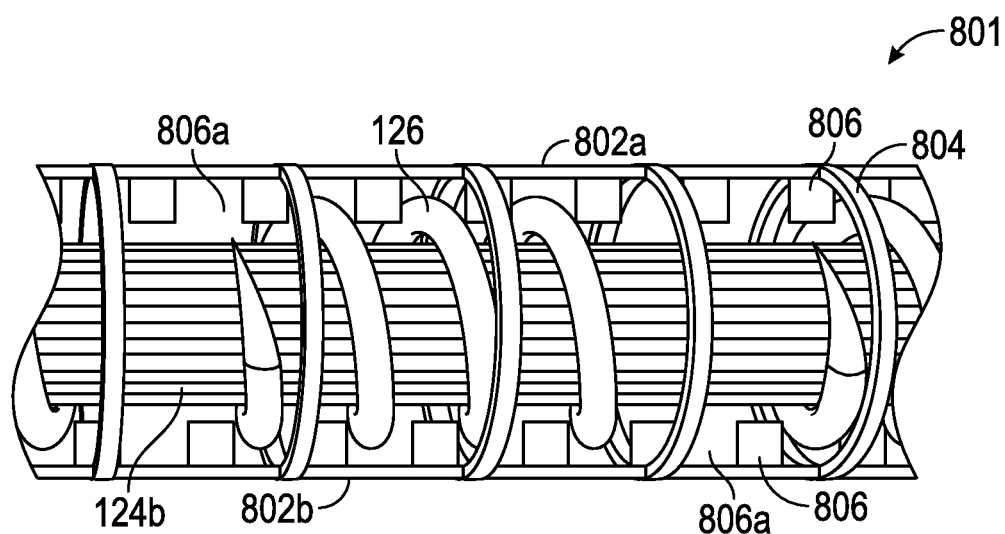
Figure 8B:
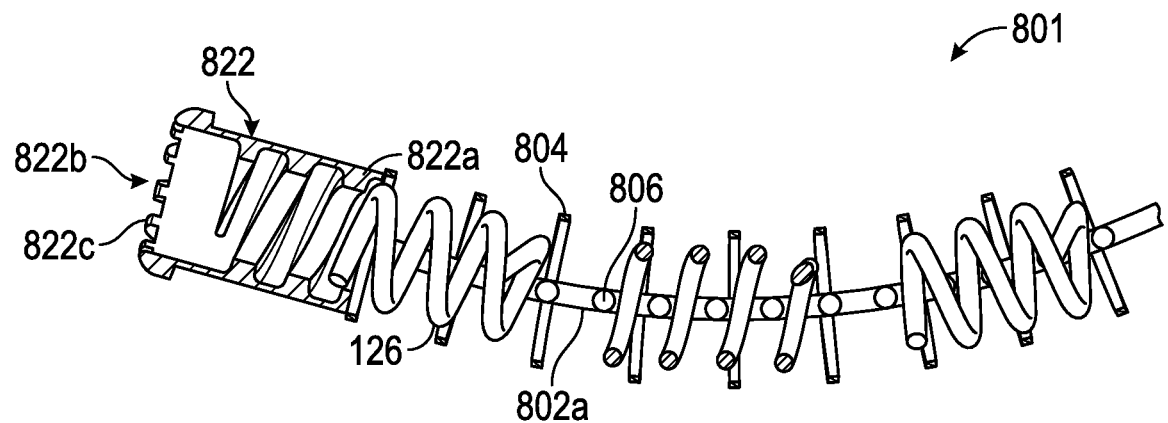

FIGS. 8, 8A and 8B depict a distal end portion of another example multi-fire fastener applier in accordance with this disclosure. This multi-fire fastener applier can include a construction of some features and components similar to those discussed with reference to the multi-fire fastener appliers discussed with respect to previous FIGURES. Thus, in some cases the multi-fire applier can have a handle that includes a battery powered motor, control circuit, first and second control buttons, indicators and functionality as previously discussed. In other cases components may be hand actuated. In some cases, applier can be a single use component that is supplied to the user within a package in a sterile condition with the fasteners preloaded therein. Additionally, multi-fire applier can be provided to users in a kit along with other components, including, e.g., a supply of fasteners, and a cassette for holding and enabling the fasteners to be loaded into the applier.

In the example illustrated in FIGS. 8 and 8B, a distal end portion of the multi-fire applier includes a fastener delivery shaft 801 that is bent in preparation for delivery of the plurality of fasteners 126. The delivery shaft 801 includes a rigid sheath 820 (shown partially removed in FIG. 8) and driver 824. FIGS. 8 and 8B also illustrate a fastener cartridge 822 at a distal end.

FIG. 8 illustrates that the driver 824, fastener cartridge 822, are radially inwardly nested within the sheath 820 such that fastener cartridge 822 is disposed within sheath 820 and the driver 824 is disposed within the cartridge 822 and/or sheath 820. An internal assembly 802 is disposed within the sheath 820 proximal of the fastener cartridge 822 and is sized and configured to hold a plurality of fasteners 126 in stacked relationship along the long axis of delivery shaft 801.

Referring to FIG. 8, sheath 820 is fabricated from a rigid material. The "rigidity" of sheath 820, as used in this disclosure, refers to the ability of sheath 820 to withstand the force applied by a physician to resolve the force of implanting one of fasteners 126. For example, sheath 820 may need to be strong enough, e.g., have sufficient column strength to withstand the generally axial resolution force without buckling or being otherwise structurally compromised. A variety of biocompatible metals, plastics, or ceramics can be used to fabricate sheath 820, including, e.g., stainless steel, nickel-titanium (Nitinol), etc.

The construction of fastener cartridge 822 is similar to fastener cartridge 122 (FIG. 1B), and thus, the fastener cartridge 822 includes a plurality of internal threads 822a. In examples including helical fastener 126, threads 822a can be helical threads with a pitch and diameter that corresponds to the pitch and diameter of fastener 126 such that fastener 126 can be threaded through cartridge 822, to move a fastener 126 further distally in the delivery process. Cartridge 822 also includes crenellations 822c, which can decrease slipping of distal end 822b on the wall of the prosthesis against which multi-fire applier is forced during implantation. Unlike cartridge 122, cartridge 822 can comprise only a distal end portion of the applier. Proximal of the cartridge 822 and within the sheath 820 is disposed the internal assembly 802, which is partially illustrated due to the removal of a portion of the sheath 820 in FIG. 8. The assembly 802 includes a first member 802a, a second member 802b (not shown in FIG. 8 but illustrated in FIG. 8A), hoops 804, and projections 806.

The assembly 802 of FIGS. 8 and 8A has the first member 802a arranged substantially along a neutral axis of the delivery shaft 801. The second member 802b (FIG. 8A) is also disposed substantially along the neutral axis. The hoops 804 are spaced from one another and couple to and extend between both the first member 802a and the second member 802b. The components of the assembly 802, (e.g., first member 802a, hoops 804, etc.) can be constructed of flexible but sufficiently rigid biocompatible metals, plastics, or ceramics including, e.g., stainless steel, nickel-titanium (Nitinol), etc.

FIG. 8A illustrates that a first number of cylindrically shaped projections 806 are coupled to the first member 802a and a second number of cylindrically shaped projections 806 are coupled to the second member 802b. The projections 806 extend inward toward the driver 824 (in particular intermediate portion 824b) from the first member 802a and the second member 802b (FIG. 8A). The projections 806 provide a ladder structure that has a pitch corresponding to that of the fasteners 126. The projections 806 and spaces 806a in concert with the driver 824 act to feed the fasteners 126 forward toward the distal end of the delivery shaft 801 to fastener cartridge 822. As will be discussed, because spaces 806a occur along the neutral axis they comprise substantially a same sized space relative to one another. This allows for advancement of the fastener 126 even if the delivery shaft 801 is bent as shown in FIGS. 8 and 8B or straight (FIG. 8A) as projections 806 will not act to impinge upon the fastener 126 even when the delivery shaft 801 is bent.

As shown in FIG. 8, the driver 824 includes a "D" shaped elongated shaft with planar face 824a along a distal end and extending to the intermediate portion 824b of the driver 824. In general, the driver 824 is shaped to fit within the inner diameters of fasteners 126. Additionally, driver 824 is configured to be disposed such that planar face 824*a* engages cross-bars 204 (FIG. 2A) of the fasteners 126 to transmit torque from driver 824 to fasteners 126. A variety of biocompatible metals, plastics, or ceramics can be used to fabricate driver 824, including, e.g., stainless steel, nickel-titanium (Nitinol), etc.

As shown in FIG. 8, the distal end portion of the driver 824 can be of a solid construction. However, the intermediate portion 824*b* of the driver 824 can be constructed of a braided cable, allowing for greater flexibility in the portion of the delivery shaft 801 that experiences the greatest degree of bending. The intermediate portion 824*b* can connect to a shaft portion 824*c* of the driver 824 proximal of the internal assembly 802 in some cases. The length of the intermediate portion 824*b* and the assembly 802 can be determined by the number of fasteners 126 to be retained therein.

Referring to FIGS. 8, 8A, and 8B the assembly 802 can include components such as the first member 802*a*, the second member 802*b*, the projections 806, and corresponding spaces 806*a* (FIG. 8A) arranged along the neutral axis of the delivery shaft 801. Thus, the projections 806 are arranged perpendicular to a bend axis of the delivery shaft 801. Thus, the projections 806 can always have substantially a same (constant) spacing with respect to one another even in a deflected portion of the delivery shaft 801. Similarly, spaces 806*a* have a substantially similar size. This allows for the pitch between the projections 806 to be maintained.

Figure 9:
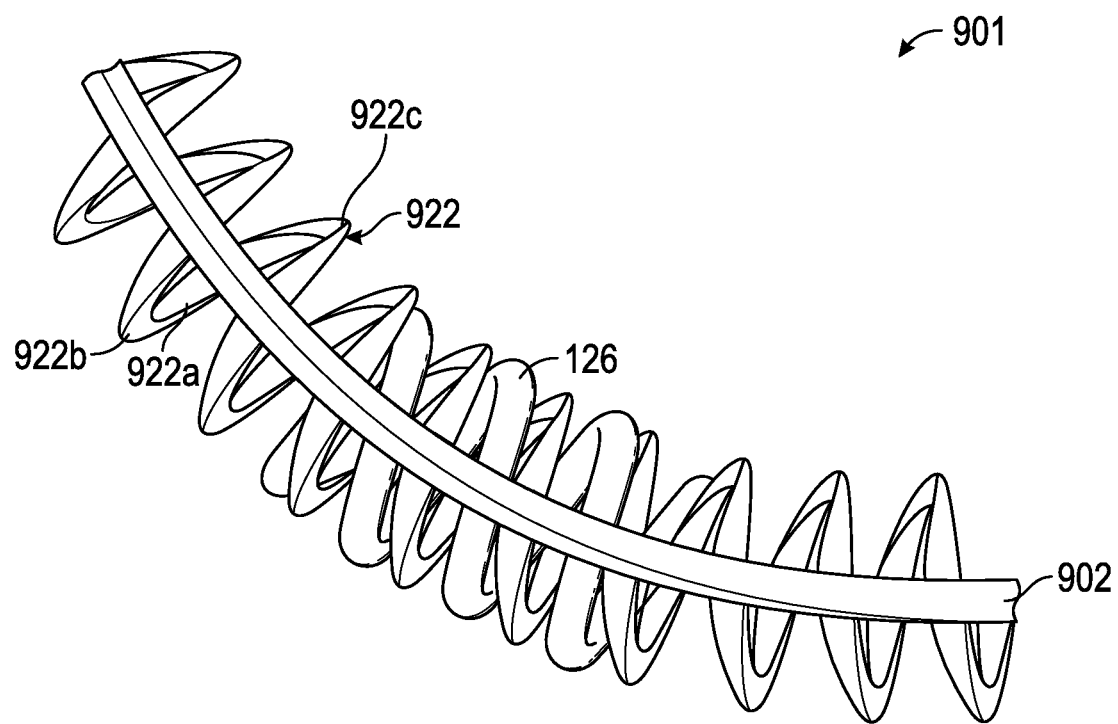
FIG. 9 depicts an example advancement mechanism in accordance with this disclosure.

FIG. 9 illustrates a distal end portion of another example multi-fire fastener applier in accordance with this disclosure. This multi-fire fastener applier can include a construction of some features and components similar to those discussed with reference to the multi-fire fastener appliers discussed with respect to previous FIGURES. Thus, in some cases the multi-fire applier can have a handle that includes a battery powered motor, control circuit, first and second control buttons, indicators and functionality as previously discussed. In other cases components may be hand actuated. In some cases, applier can be a single use component that is supplied to the user within a package in a sterile condition with the fasteners preloaded therein. Additionally, multi-fire applier can be provided to users in a kit along with other components, including, e.g., a supply of fasteners, and a cassette for holding and enabling the fasteners to be loaded into the applier.

In the example illustrated in FIG. 9, only a portion of a fastener delivery shaft 901 is shown comprising a support member 902 and a helical track 922. Although not illustrated, helical track 922 can be positioned proximal the fastener cartridge to communicate therewith. In FIG. 9, the sheath and the driver are not illustrated. However, the member 902 and a helical track 922 could be utilized in combination with those features in some examples.

Member 902 extends substantially along a neutral axis of the delivery shaft 901. Helical track 922 is coupled to the support member 902. The member support 902 provides support to the helical track 922. Although only one fastener 126 is shown in FIG. 9, the helical track 922 is adapted to receive multiple fasteners 126 therein and can act as a ladder feature for the advancement of the fasteners 126. Thus, the helical track 922 has a pitch adapted to correspond with that of the fasteners 126 to allow for passage of the fasteners therealong.

Helical track 922 includes a neutral axis portion 922*a*, a first portion 922*b*, and a third portion 922*c*. The neutral axis portion 922*a* has a larger cross-sectional area as compared with the first portion 922*b* and second portion 922*c*. The first portion 922*b* and the second portion 922*c* are provided with a smaller cross-sectional area to maintain clearance sufficient to allow passage of the fastener 126 when the fastener delivery shaft 901 is bent.

FIG. 10 shows a distal end portion of yet another example multi-fire fastener applier in accordance with this disclosure. This multi-fire fastener applier can include a construction of some features and components similar to those discussed with reference to the multi-fire fastener appliers discussed with respect to previous FIGURES. Thus, in some cases the multi-fire applier can have a handle that includes a battery powered motor, control circuit, first and second control buttons, indicators and functionality as previously discussed. In other cases components may be hand actuated. In some cases, applier can be a single use component that is supplied to the user within a package in a sterile condition with the fasteners preloaded therein. Additionally, multi-fire applier can be provided to users in a kit along with other components, including, e.g., a supply of fasteners, and a cassette for holding and enabling the fasteners to be loaded into the applier. Thus, the multi-fire applier of FIG. 10 includes a fastener delivery shaft 1001. As shown partially removed in FIG. 10, the delivery shaft 1001 includes a rigid sheath 1020 and driver 1024. FIG. 10 also illustrates a fastener cartridge 1022, an advancement component 1006, and storage members 1008*a*, 1008*b*, 1008*c*, and 1008*d*.

The construction of the sheath 1020, fastener cartridge 1022, and driver 1024 has been discussed previously, and therefore, will not be discussed in extensive detail. Driver 1024 can include the "D" shaped elongated shaft with planar face 1024*a*, the intermediate portion 1024*b* again with planar face 1024*a*, and shaft portion 1024*c*.

The storage member 1008*a*, 1008*b*, 1008*c*, and 1008*d* are disposed within the sheath 1020 and can be disposed along the intermediate portion 1024*b*. Although four storage members are illustrated in FIG. 10, the number of storage features can vary depending upon the number of fasteners 126 desired to be delivered. Each storage member 1008*a*, 1008*b*, 1008*c*, and 1008*d* can comprise an internal cassette that houses one or more fasteners 126. Each storage member 1008*a*, 1008*b*, 1008*c*, and 1008*d* can be constructed hollow internal storage volume configured to receive one or more of the fasteners 126. The storage members 1008*a*, 1008*b*, 1008*c*, and 1008*d* are spaced from one another to allow for flexibility of the delivery shaft 1001.

The advancing component 1006 is adapted to be moveable relative to the sheath 1020, driver 1024, and storage members 1008*a*, 1008*b*, 1008*c*, and 1008*d* and can be a tube constructed of a sufficiently rigid but flexible material that allows for bending of the fastener delivery shaft 1001. The advancing component 1006 can be utilized to contact and apply a push force to the fasteners 126. This can be achieved because the storage members 1008*a*, 1008*b*, 1008*c*, and 1008*d* are hollow and are adapted to receive the advancing component 1006 therein. The push force exerted by the advancing component 1006 on the fasteners 126 can be sufficient to engage the fasteners 126 with a cantilever barb, hook, or similar transfer feature at a proximal end of each storage member 1008*a*, 1008*b*, 1008*c*, and 1008*d*. A cross-sectional view of a storage member 1008 representative of storage members 1008*a*, 1008*b*, 1008*c*, 1008*d* having a cantilever barb, hook, or similar transfer feature 1030 at a proximal end is illustrated in FIG. 10A. Once the fastener 126 engages the transfer feature, the fastener 126 is able to advance to the next most distal storage member until the fastener cartridge 1022 is reached. Although illustrated as a mechanical member in FIG. 10, in some examples the advancing component can comprise compressed gas or fluid, a spring, etc. The advancing member can be driven by a battery or motor actuated in some instances. In other instances, the movement of the advancing member can be the result of knobs or other features on the fastener applier.

One or more of the embodiments of the multi-fire fastener applier discussed herein can include a sensor making use of electric resistance or capacitance in the sheath to detect the position of the fasteners within the distal end of the fastener applier. In other cases, the sensor(s) may have a mechanical feature in the sheath that can provide a calibrated resistance to the fasteners during advancement into a start position. Additionally and or alternatively, the fasteners may be detected through torque sensing on the driver and/or other drive components (e.g., drive shaft, etc.) These and other sensing configurations and techniques can be used in combination with the deployment mechanisms and functions previously discussed for deployment control of the fasteners.

Various examples have been described. These and other examples are within the scope of the following claims.

We claim:

1. A fastener delivery system comprising:
   a handle; and
   a fastener delivery shaft extending distally from the handle, the fastener delivery shaft comprising:
      a sheath;
      hollow storage members within the sheath, the hollow storage members being configured to receive helical fasteners therein, wherein the hollow storage members are spaced apart from one another by annular spaces; and
      an advancement component comprising a tube, the advancement component moveable relative to the storage members, the storage members configured to receive the advancement component therein.

2. The fastener delivery system of claim 1 wherein the advancement component is located within the sheath.

3. The fastener delivery system of claim 1 wherein the annular spaces in between the hollow storage members allow for flexibility in the fastener delivery shaft.

4. The fastener delivery system of claim 1 wherein the advancement component is configured to exert an advancement force on the helical fasteners.

5. The fastener delivery system of claim 4, wherein the fastener delivery shaft further comprises a fastener cartridge, wherein the advancement force is configured to move the helical fasteners towards the fastener cartridge.

6. The fastener delivery system of claim 1, wherein proximal portions of the storage members have features that facilitates transfer of the helical fasteners from the storage members.

7. The fastener delivery system of claim 1, wherein the fastener delivery shaft further comprises a driver shaft within the sheath.

8. The fastener delivery system of claim 7, wherein the driver shaft comprises a flexible intermediate portion.

9. The fastener delivery system of claim 8, wherein the hollow storage members are disposed along the intermediate portion of the driver shaft and the intermediate portion of the driver shaft is configured to pass through the helical fasteners.

10. A fastener delivery system comprising:
    a handle; and
    a fastener delivery shaft extending distally from the handle, the fastener delivery shaft comprising:
       a fastener cartridge comprising a plurality of internal threads;
       hollow storage members proximal of the fastener cartridge, wherein the hollow storage members are spaced apart from one another by annular spaces;
       helical fasteners within the hollow storage members; and
       an advancement component comprising a tube, the advancement component moveable to push the helical fasteners.

11. The fastener delivery system of claim 10, wherein the hollow storage members comprise:
    hollow internal storage volumes configured to receive the helical fasteners therein; and
    transfer features.

12. The fastener delivery system of claim 11, wherein the advancement component pushes the helical fasteners into engagement with the transfer features.

13. The fastener delivery system of claim 10, wherein the fastener delivery shaft further comprises a sheath, the hollow storage members and the advancement component being within the sheath.

14. The fastener delivery system of claim 10, wherein the fastener delivery shaft further comprises a driver shaft within the hollow storage members.

15. A method comprising:
    loading a helical fastener within a proximal storage member of a delivery shaft;
    moving an advancement component to contact the helical fastener, the advancement component comprising a tube;
    applying a push force to the helical fastener from the advancement component to engage the helical fastener with a transfer feature at a proximal end of the proximal storage member; and
    advancing the helical fastener from the proximal storage member to one or more distal storage members distal of the proximal storage member.

16. The method of claim 15 further comprising advancing the helical fastener from the one or more distal storage members to a fastener cartridge comprising a plurality of internal threads.

17. The method of claim 16 further comprising advancing the helical fastener from the fastener cartridge and into tissue.

18. The method of claim 15 wherein the loading a helical fastener further comprises loading a plurality of helical fasteners including the helical fastener within the proximal storage member and the one or more distal storage members.

* * * * *